US00PP26070P2

(12) United States Plant Patent
Verschoor

(10) Patent No.: US PP26,070 P2
(45) Date of Patent: Nov. 10, 2015

(54) ***PHLOX* PLANT NAMED 'VERSOLDBLUE'**

(50) Latin Name: *Phlox paniculata*
Varietal Denomination: Versoldblue

(71) Applicant: Janus Verschoor, Haarlem (NL)

(72) Inventor: Janus Verschoor, Haarlem (NL)

( * ) Notice: Subject to any disclaimer, the term of this patent is extended or adjusted under 35 U.S.C. 154(b) by 106 days.

(21) Appl. No.: 13/998,909

(22) Filed: Dec. 19, 2013

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — C. A. Whealy

(57) ABSTRACT

A new and distinct cultivar of *Phlox* plant named 'Versoldblue', characterized by its upright and relatively compact plant habit; freely flowering habit; large inflorescences with purple violet, violet and white-colored flowers; long flowering period; good garden performance and resistance to Powdery Mildew.

2 Drawing Sheets

Botanical designation: *Phlox paniculata.*
Cultivar denomination: 'VERSOLDBLUE'.

BACKGROUND OF THE INVENTION

The present invention relates to a new and distinct cultivar of *Phlox* plant, botanically known as *Phlox paniculata* and hereinafter referred to by the name 'Versoldblue'.

The new *Phlox* plant is a product of a planned breeding program conducted by the Inventor in Haarlem, The Netherlands. The objective of the breeding program was to create new compact and freely-flowering *Phlox* plants with attractive flower colors.

The new *Phlox* plant originated from a cross-pollination made by the Inventor in 2007 in Haarlem, The Netherlands, of two unnamed seedling selections of *Phlox paniculata,* not patented. The new *Phlox* plant was discovered and selected by the Inventor as a single flowering plant from within the progeny of the stated cross-pollination in a controlled environment in Haarlem, The Netherlands in 2009.

Asexual reproduction of the new *Phlox* plant by cuttings in a controlled environment in Haarlem, The Netherlands since 2009 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Versoldblue'. These characteristics in combination distinguish 'Versoldblue' as a new and distinct *Phlox* plant:

1. Upright and relatively compact plant habit.
2. Freely flowering habit.

3. Large inflorescences with purple violet, violet and white-colored flowers.
4. Long flowering period.
5. Good garden performance.
6. Resistance to Powdery Mildew.

Plants of the new *Phlox* and the parent selections differ primarily in the following characteristics:

1. Plants of the new *Phlox* are shorter and more compact than plants of the parent selections.
2. Plants of the new *Phlox* and the parent selections differ in inflorescence shape.
3. Plants of the new *Phlox* are stronger and more resistant to Powdery Mildew than plants of the parent selections.

Plants of the new *Phlox* can be compared to plants of *Phlox paniculata* 'Laura', not patented. In side-by-side comparisons conducted in Haarlem, The Netherlands, plants of the new *Phlox* and 'Laura' differed in the following characteristics:

1. Plants of the new *Phlox* were shorter and more compact than plants of 'Laura'.
2. Plants of the new *Phlox* were more freely flowering than plants of 'Laura'.
3. Plants of the new *Phlox* had larger inflorescences than plants of 'Laura'.
4. Plants of the new *Phlox* and 'Laura' differed in flower color as plants of 'Laura' had lilac and white-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Versoldblue' grown in a container.

The photograph on the second sheet is a close-up view of typical flowers of 'Versoldblue'.

DETAILED BOTANICAL DESCRIPTION

The aforementioned photographs and following observations, measurements and values describe plants grown during the late summer and early autumn in 1.5-liter containers in an outdoor nursery in Haarlem, The Netherlands and under cultural practices typical of commercial *Phlox* production. During the production of the plants, day temperatures ranged from 14° C. to 28° C. and night temperatures ranged from 6° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Phlox paniculata* 'Versoldblue'.

Parentage:

*Female, or seed, parent*.—Unnamed seedling selection of *Phlox paniculata,* not patented.

*Male, or pollen, parent*.—Unnamed seedling selection of *Phlox paniculata,* not patented.

Propagation:

*Type*.—By cuttings.

*Time to initiate roots, summer*.—About three weeks at temperatures about 20° C.

*Time to produce a rooted plant, summer*.—About six weeks at temperatures about 20° C.

*Root description*.—Fine, fibrous; white in color.

*Rooting habit*.—Moderately freely branching; medium density.

Plant description:

*Plant and growth habit*.—Herbaceous perennial; upright and relatively compact plant habit; broad inverted triangle; low vigor.

*Plant height*.—About 35.3 cm.

*Plant width* (*spread*).—About 28.5 cm.

*Lateral branches*.—Length: About 21.9 cm. Diameter: About 4 mm. Internode length: About 2.5 cm. Strength: Strong. Aspect: Upright to about 30° from vertical. Texture: Smooth, glabrous. Color: Close to 143B; at the nodes, close to 200B.

Leaf description:

*Arrangement*.—Opposite, simple.

*Length*.—About 8.3 cm.

*Width*.—About 3.8 cm.

*Shape*.—Ovate to elliptic, carinate.

*Apex*.—Acute.

*Base*.—Truncate.

*Margin*.—Entire, revolute.

*Texture, upper and lower surfaces*.—Smooth, glabrous.

*Venation pattern*.—Pinnate.

*Color*.—Developing leaves, upper surface: Close to 143A; at the margins, tinged with close to N186A. Developing leaves, lower surface: Close to 146C. Fully expanded leaves, upper surface: Between N137A and 147A; venation, close to 144A. Fully expanded leaves, lower surface: Close to 147B; venation, close to 144B to 144C.

*Petioles*.—Length: About 2 mm. Diameter: About 2 mm by 3 mm. Texture, upper and lower surfaces: Smooth, glabrous. Color, upper and lower surfaces: Close to 144B.

Flower description:

*Flower type and flowering habit*.—Single rotate and salverform flowers arranged in compound terminal panicles; flowers face mostly upright to outwardly; panicles roughly hemispherical in shape; freely flowering habit with about 100 flowers developing per inflorescence.

*Fragrance*.—Moderately fragrant; sweet, pleasant.

*Natural flowering season*.—Plants begin flowering about nine months after planting; long flowering period, plants flower continuously from July through September in The Netherlands.

*Postproduction longevity*.—Flowers last about ten days on the plant; flowers not persistent.

*Flower buds*.—Height: About 2.4 cm. Diameter: About 5 mm. Shape: Narrowly elliptic to narrowly oblanceolate. Color: Close to N88B to N88D and 90B; towards the base, close to 83A; immature calyx, close to 145B tinged with close to N186C.

*Inflorescence height*.—About 13.3 cm.

*Inflorescence diameter*.—About 11.7 cm.

*Flower diameter*.—About 3.6 cm.

*Flower depth*.—About 2.8 cm.

*Petals*.—Quantity per flower: Typically five in a single whorl; petals fused at the base into a narrow tube. Length: About 4 cm; lower 2.4 cm fused. Lobe width: About 2 cm. Shape: Spatulate. Apex: Rounded. Margin: Entire. Texture, upper and lower surfaces: Smooth, glabrous; slightly velvety. Color: When opening, upper surface: Close to N82A and 83B to 83D; towards the base, close to NN155C; throat, close to 79D. When opening, lower surface: Close to 83D, 84D and 86C to 86D; tube, close to 79C. Fully opened, upper surface: Close to N82C and 83D; towards the base, close to NN155D; throat, close to 79D; with development, color becomes closer to between 84A and 86D. Fully opened, lower surface: Close to 83D, 84D and 86C to 86D; tube, close to 79C.

*Sepals*.—Quantity per flower: Typically five in a single whorl, fused towards the base; calyx, campanulate. Length: About 1.1 cm. Width: About 2 mm. Shape: Lanceolate. Apex: Narrowly apiculate. Margin: Entire. Texture, upper and lower surfaces: Smooth, glabrous. Color: When opening and fully opened, upper surface: Close to 145A tinged with close to N186C. When opening and fully opened, lower surface: Close to 145B tinged with close to N186C.

*Peduncles*.—Length, primary peduncles: About 9.8 cm. Diameter, primary peduncles: About 2 mm. Length, secondary peduncles: About 3.7 cm. Diameter, secondary peduncles: About 1.5 mm. Aspect, primary peduncles: Erect. Aspect, secondary peduncles: About 35° from vertical. Strength: Strong. Texture: Smooth, glabrous. Color: Close to 145A; distally, tinged with close to 184B.

*Pedicels*.—Length: About 4 mm. Diameter: About 1 mm. Angle: About 30° from the peduncle axis. Strength: Strong. Texture: Smooth, glabrous. Color: Close to 145A.

*Reproductive organs*.—Stamens: Quantity per flower: Typically five; filaments fused with petals. Filament length: About 1 mm. Filament color: Close to 145C. Anther length: About 2 mm. Anther shape: Oblong. Anther color: Close to 5D. Pollen amount: Moderate.

Pollen color: Close to 11D. Pistils: Quantity per flower: One. Pistil length: About 2 cm. Stigma shape: Cleft, three-parted. Stigma color: Close to 150B. Style length: About 1.8 cm. Style color: Close to 150C. Ovary color: Close to 143A to 143B.

*Seeds and fruits*.—Seed and fruit development have not been observed on plants of the new *Phlox*.

Garden performance: Plants of the new *Phlox* have been observed to have good garden performance and tolerate rain, wind, high temperatures about 35° C. and to be winter hardy to USDA Hardiness Zone 6.

Disease & pest resistance: Plants of the new *Phlox* have been observed to be resistant to Powdery Mildew; plants of the new *Phlox* have not been observed to be resistant to pests and other pathogens common to *Phlox* plants.

It is claimed:

1. A new and distinct *Phlox* plant named 'Versoldblue' as illustrated and described.

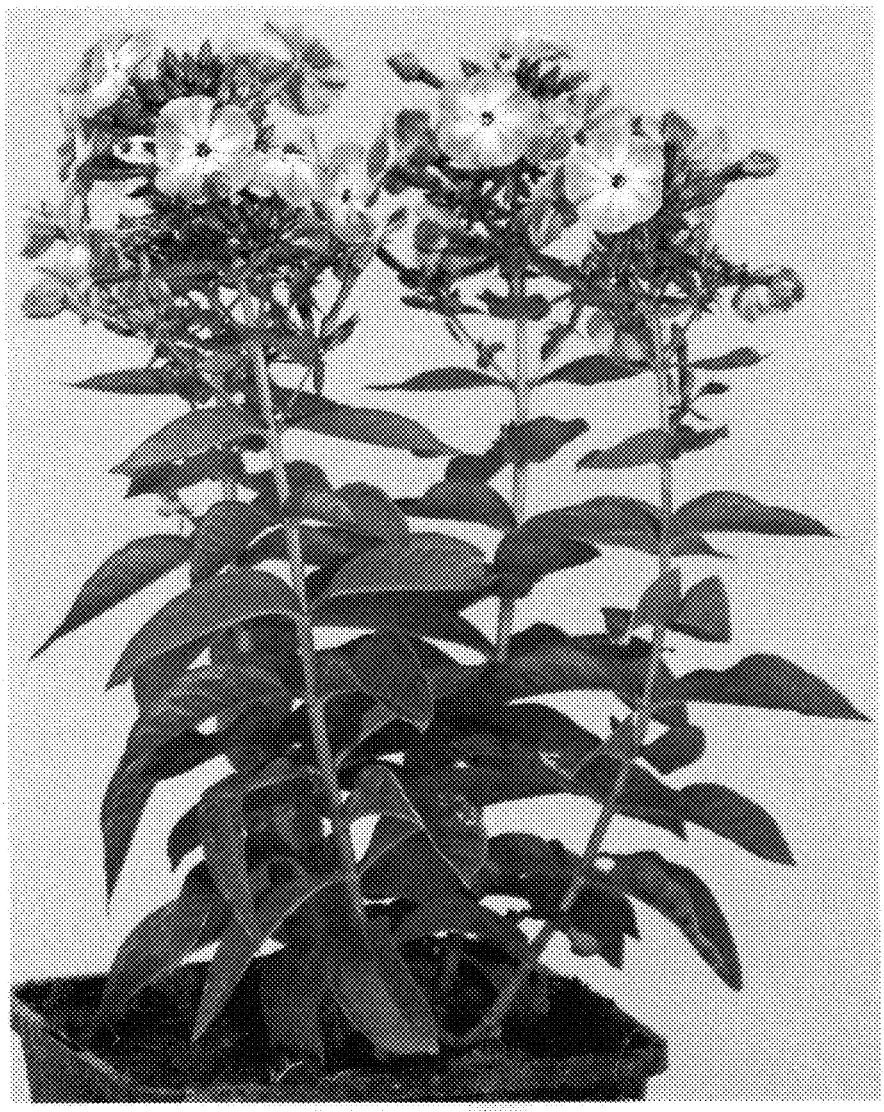

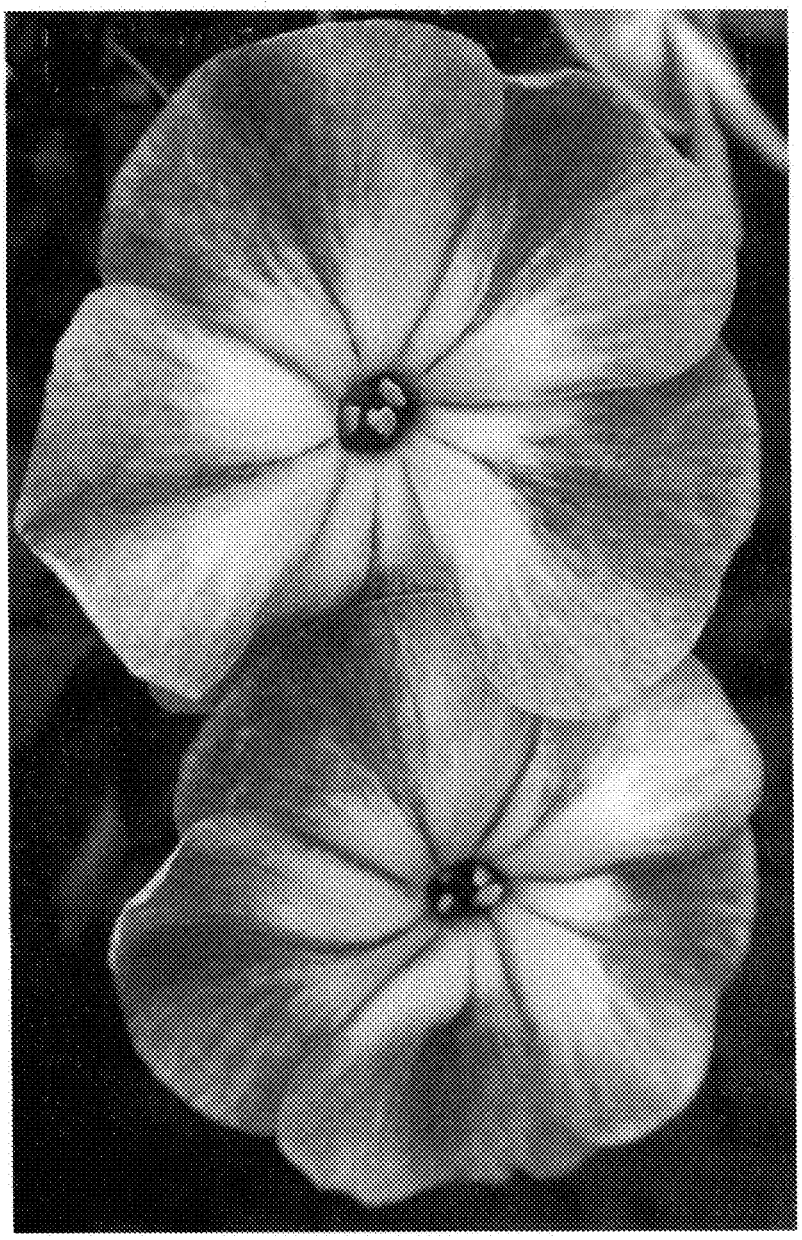

* * * * *